US012702307B2

(12) United States Patent
Sinusas et al.

(10) Patent No.: US 12,702,307 B2
(45) Date of Patent: Aug. 11, 2026

(54) NON-INVASIVE STRESS IMAGING METHODS OF DIAGNOSING PERIPHERAL ARTERIAL DISEASE VIA DYNAMIC PET

(71) Applicants: Jubilant DraxImage inc., Montreal (CA); Yale University, New Haven, CT (US)

(72) Inventors: Albert Sinusas, New Haven, CT (US); Norman LaFrance, Yardley, PA (US)

(73) Assignee: Jubilant Draximage Inc. (CA)

( * ) Notice: Subject to any disclaimer, the term of this patent is extended or adjusted under 35 U.S.C. 154(b) by 425 days.

(21) Appl. No.: 18/320,720

(22) Filed: May 19, 2023

(65) Prior Publication Data

US 2023/0284910 A1 Sep. 14, 2023

Related U.S. Application Data

(63) Continuation-in-part of application No. PCT/US2022/033110, filed on Jun. 10, 2022.

(Continued)

(51) Int. Cl.
*A61B 5/02* (2006.01)
*A61B 5/00* (2006.01)

(Continued)

(52) U.S. Cl.
CPC ........ *A61B 5/02007* (2013.01); *A61B 5/0073* (2013.01); *A61B 5/02755* (2013.01); *A61B 5/055* (2013.01)

(58) Field of Classification Search
None
See application file for complete search history.

(56) References Cited

U.S. PATENT DOCUMENTS

2008/0042067 A1* 2/2008 Rousso ................ A61B 6/4258 250/363.04
2008/0128626 A1 6/2008 Rousso et al.

(Continued)

FOREIGN PATENT DOCUMENTS

WO PCT/US22/33110 12/2022

OTHER PUBLICATIONS

Chou et al., “Clinical Applications for Radiotracer Imaging of Lower Extremity Peripheral Arterial Disease and Critical Limb Ischemia”, (Apr. 2020) Mol Imaging Biol. Apr. 2020;22(2):245-255. (Year: 2020).*

(Continued)

*Primary Examiner* — Keith M Raymond
*Assistant Examiner* — Ashish S. Jasani
(74) *Attorney, Agent, or Firm* — William D. Hare; McNeely, Hare & War, LLP

(57) ABSTRACT

The present invention provides a method of determining whether a subject is suffering or at a risk of developing a peripheral arterial disease via Positron Emitting Tomography (PET) imaging technology. The method comprises administering a PET radionuclide into the subject via automated generation and/or infusion system, performing PET scan of the region of interest, automated assessment of the PET images, performing assessment and suggesting the most appropriate therapeutic and/or management options for the patients based on the severity score, provides an assessment of regional lower proximity perfusion and perfusion reserve, and/or regional and mean standardized uptake values (SUVs). More particularly, the method of image processing identifies the regional differences in SMP (Skeletal muscle perfusion) and SMPR (Skeletal muscle perfusion reserve) across calf muscles at rest and cuff-induced hyperemia.

16 Claims, 9 Drawing Sheets

Related U.S. Application Data

(60) Provisional application No. 63/209,508, filed on Jun. 11, 2021.

(51) Int. Cl.
*A61B 5/0275* (2006.01)
*A61B 5/055* (2006.01)

(56) References Cited

U.S. PATENT DOCUMENTS

2015/0165074 A1 6/2015 Lazewatsky et al.
2015/0230762 A1* 8/2015 Alpert ................ A61K 51/0459 600/425
2015/0363948 A1* 12/2015 Leahy .................... A61B 6/504 600/425
2018/0018768 A1* 1/2018 Hsu ........................ A61B 6/037
2018/0242885 A1 8/2018 Naqvi et al.
2020/0029925 A1* 1/2020 Saillant .................. A61B 6/486
2020/0312474 A1 10/2020 Lefort et al.

OTHER PUBLICATIONS

Stacy et al., “Radiotracer Imaging of Peripheral Vascular Disease” (Sep. 2015), Journal of Nuclear Medicine Technology Sep. 2015, 43 (3) 185-192. (Year: 2015).*

Santo Dellegrottaglie et al., Technology Insight: magnetic resonance angiography for the evaluation of patients with peripheral artery disease, Nature Reviews Cardiology 4, 677-687 (2007) https://doi.org/10.1038/ncpcardio1035 (Abstract and Key Points only).

* cited by examiner

Figure 1a

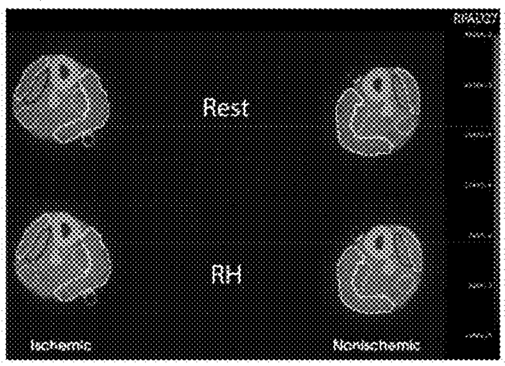

Figure 1b

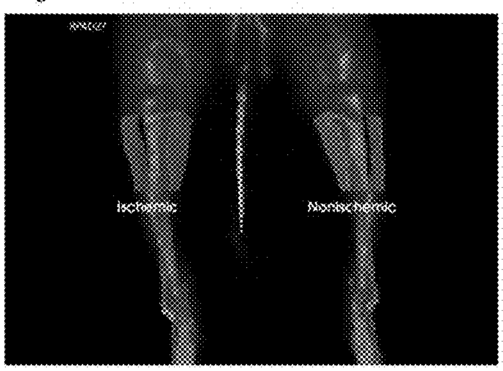

Figure 1c

Rest Ischemic   Rest Non-Ischemic   RH Ischemic   RH Non-Ischemic mean SUVs (g/mL)

2.5
2
1.5
1
0.5
0

GC   PLA   SOL   TA   EDL   PER

Figure 1d

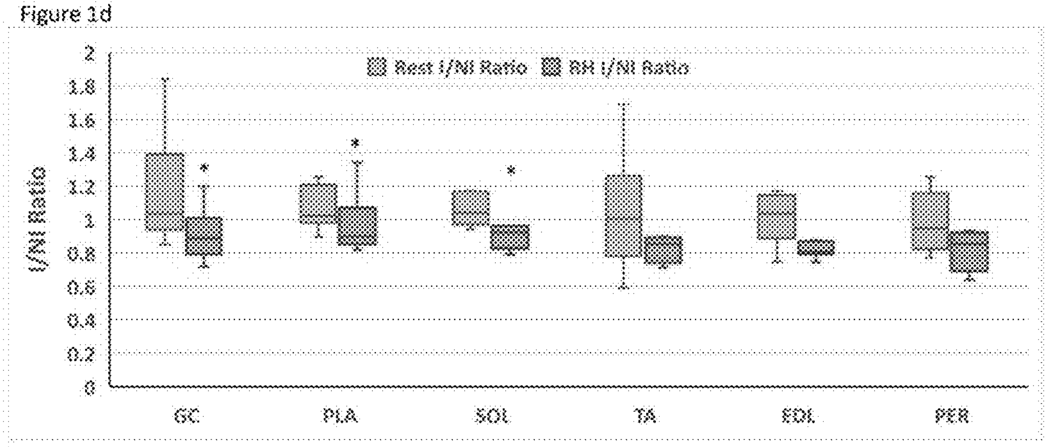

Figure 1a. Representative transaxial rest and hyperemic Rb-82 PET images at mid-calf with muscles segmented; Figure 1b. Representative 3D segmentation volumes of interest (VOIs) on lower extremity Rb-82 PET images; Figure 1c. Average SUVs in ischemic and non-ischemic limbs for individual muscles; Figure 1d. Ratio of ischemic to non-ischemic SUVs at rest and reactive hyperemia. * P<0.05 versus rest

Fig. 8a-d

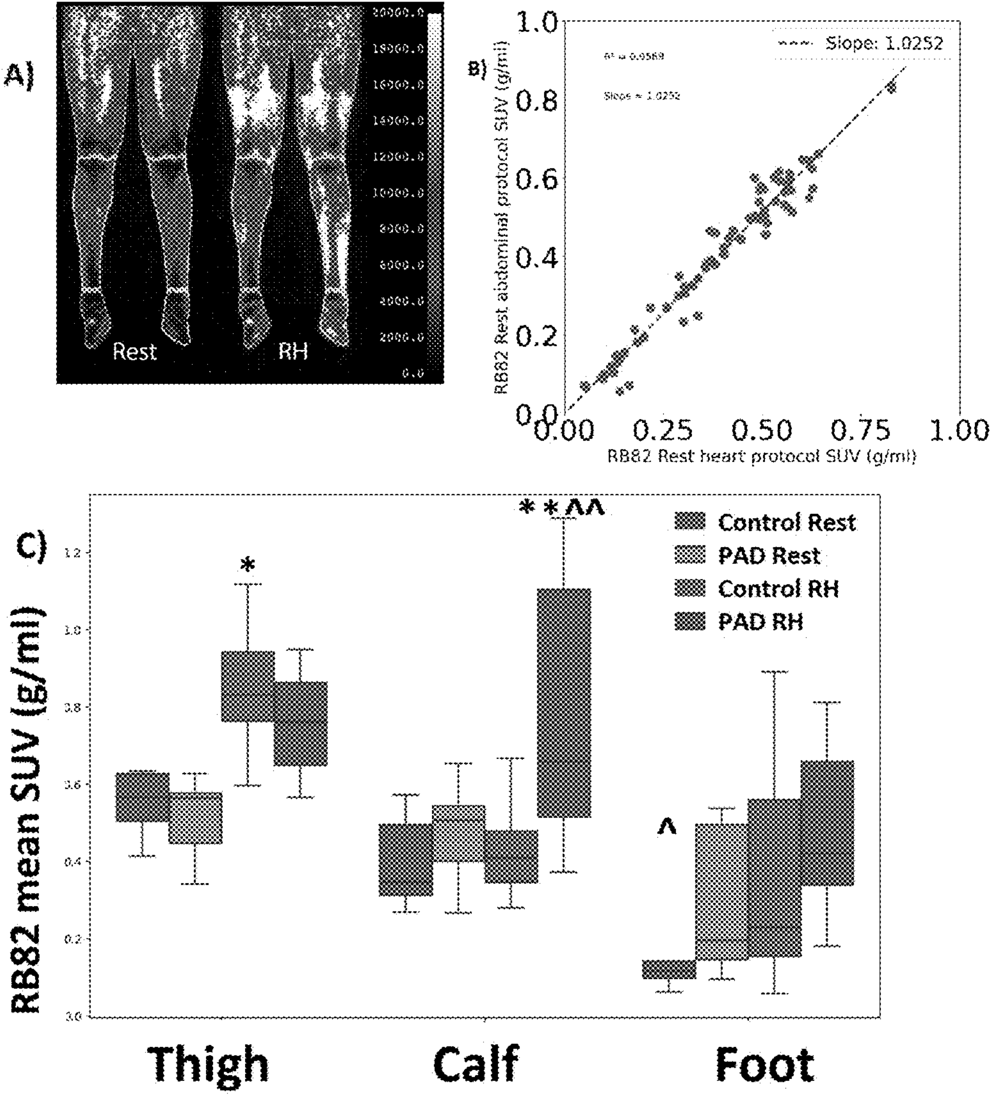

Figure 1A: Rb image of a PAD patient during rest and cuff-induced hyperemia. Decreased perfusion in right lower extremity seen during RH. Figure 1B: Scatter plots of Rb obtained with heart and abdomen protocol at rest and reactive hyperemia. Figure 1C: Regional Rb SUVs at rest and reactive Hyperemia. Significance is determined through post hoc Tukey analysis, comparing Control and PAD subjects at rest and RH. * Control thigh rest vs reactive hyperemia P =0.035. ** PAD calf rest vs reactive hyperemia P<0.01. ^^ PAD calf reactive hyperemia vs control calf reactive hyperemia P<0.01. ^ Control rest foot vs rest thigh P=0.035.

Fig. 9A-C

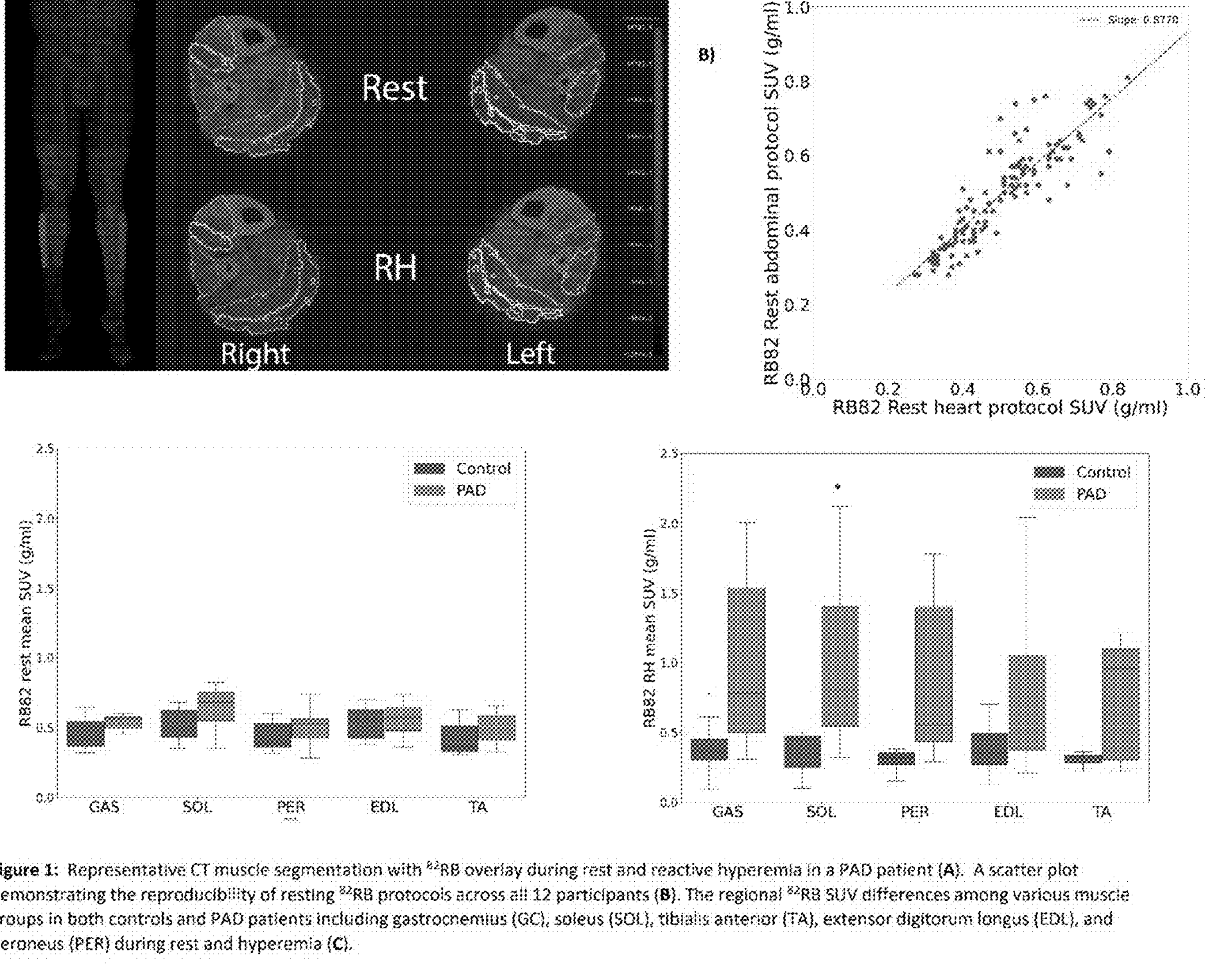
Fig. 10A-C

NON-INVASIVE STRESS IMAGING METHODS OF DIAGNOSING PERIPHERAL ARTERIAL DISEASE VIA DYNAMIC PET

TECHNICAL FIELD

The present invention relates in general to nuclear imaging and medicine, in particular, to Positron Emitting Tomography (PET) for diagnosing and/or treating peripheral arterial disease.

BACKGROUND

Peripheral arterial disease (PAD) is a progressive atherosclerotic disease of the lower limbs affecting over 8 million Americans (Virani et al., *Heart Disease and Stroke Statistics* 2021 *Update*) and advances more quickly in patients with metabolic disease like diabetes mellitus (DM), which remains a major health care issue in the United States affecting over 29 million individuals. Microvascular disease is highly prevalent in DM patients, which further complicates the evaluation and treatment of peripheral arterial disease in diabetic patients that suffer from disease of both the large vessels and microcirculation.

The conventional methods of diagnosing peripheral arterial disease include: a) physical examination, b) Ankle-brachial index (ABI), which is a common test used to diagnose PAD, but it is unable to specify exact lesion locations c) Duplex ultrasonography, which can only evaluate major blood vessels d) CT/CMR invasive angiography, which is an invasive method and it lacks quantitative tools to access the physiologic consequences and e) blood tests. None of these tests provides quantitative assessment of the blood flow in the affected part of a subject suffering from PAD.

PET agent like $^{18}$F-FDG known for atherosclerosis has a disadvantage especially in diabetic patients wherein administration of FDG can further increase the blood glucose levels and can cause problems for patient suffering from diabetes mellitus. It is known that $^{18}$F-FDG uptake is altered in patients with diabetes mellitus therefore; diabetic patients may need stabilization of blood glucose on the day preceding, and on the day of the $^{18}$F-FDG scan. Therefore, there exits an unmet and urgent need to identify a suitable PET tracer for diagnosis of peripheral arterial disease in subjects suffering from metabolic disease like diabetes mellitus.

SUMMARY

The present invention relates to novel non-invasive method of diagnosing and/or treating Peripheral Arterial Disease (PAD) in a subject.

It is an object of present disclosure to provide non-invasive method of diagnosing and/or treating peripheral arterial disease in a subject.

It is an object of present disclosure to provide non-invasive method of diagnosing and/or treating peripheral arterial disease in a subject suffering from diabetes mellitus.

It is an object of present disclosure to provide non-invasive imaging of a body part or region of interest for diagnosing and/or treating peripheral arterial disease in a subject suffering from diabetes mellitus.

It is an object of present disclosure to provide a method of non-invasive imaging of a body part or region of interest for diagnosing and/or treating peripheral arterial disease in a subject suffering from diabetes mellitus comprising administering a Positron Emission Tomography (PET) agent and imaging the region of interest.

It is an object of present disclosure to provide a method of non-invasive imaging of a body part or region of interest for identifying a risk of developing peripheral arterial disease in a subject comprising administering Rb-82 and imaging region of interest.

It is an object of present disclosure to provide a method of non-invasive imaging of a body part or region of interest for diagnosing and/or treating peripheral arterial disease in a subject suffering from diabetes mellitus comprising administering a dose of Rb-82 and imaging region of interest.

It is an object of present disclosure to diagnose and/or treat a subject suffering from or at a risk of developing peripheral arterial disease comprising administering a PET agent and performing a quantitative assessment of blood flow to the region of interest.

It is an object of present disclosure to provide a novel imaging approach and/or protocol for diagnosis of peripheral arterial disease in a subject suffering from diabetes mellitus.

It is an object of present disclosure to provide a novel imaging approach and/or protocol for diagnosis of limb ischemia in a subject.

It is an object of present disclosure to provide a novel imaging approach and/or protocol for diagnosis of limb ischemia in a subject suffering from diabetes mellitus.

It is an object of present disclosure to provide a novel imaging approach and/or protocol for identifying a subject at a risk of developing limb ischemia.

It is an object of present disclosure to provide a novel imaging approach and/or protocol for the quantitative evaluation of peripheral arterial disease in a subject suffering from a diabetes mellitus.

It is an object of present disclosure to provide a novel imaging approach and/or protocol for the quantitative evaluation of lower extremity perfusion at rest and stress for application in patients suspected of peripheral arterial disease.

It is an object of present disclosure to provide automated infusion of imaging agent into a subject for diagnosing peripheral arterial disease in a subject.

It is an object of present disclosure to provide pharmaceutical compositions and kits for imaging agent in an injectable dosage form.

It is an object of present disclosure to provide a novel kinetic compartment model or retention model for quantitative assessment of peripheral arterial disease.

It is an object of present invention to provide the severity score of disease based on the quantitative assessment of peripheral arterial disease in a subject.

It is an object of present disclosure to provide therapy options.

It is an object of the present invention to optimize and validate a dynamic Rb-82 PET rest and pharmacological stress/exercise based stress-imaging protocol for quantitative assessment of lower extremity perfusion that involves continuous bed motion (CBM) shuttle mode between imaging of the abdominal aorta (AA) and lower extremities. Imaging of the abdominal aorta will allow for the non-invasive determination of the arterial input function.

It is an object of the present invention to translate the rest/stress dynamic Rb-82 PET imaging protocol to normal subjects and patients with Diabetes Mellitus (DM) and peripheral arterial disease, using 0-15 water for clinical validation.

It is an object of the present invention to establish the most appropriate kinetic compartment model or retention model for quantitative assessment of lower extremity perfusion in patients.

The present invention concerns any of the following aspects:

In one aspect of the present invention, a method of diagnosing and/or treating a peripheral arterial disease in a subject suffering from metabolic disease comprising; calculating a dose of Rb-82 chloride to be administered to the subject; administering the calculated dose of Rb-82 chloride to a subject by automated generation and infusion system and scanning the region of interest; administering a pharmacologic stress agent and second dose protocol after resting dose infusion and scanning the region of interest; performing the assessment of images; and diagnosing peripheral arterial disease in a subject thereof.

In another aspect of the present invention, a method of diagnosing and/or treating a peripheral artery disease in a subject suffering from metabolic disease, wherein the metabolic disease is diabetes mellitus.

In another aspect of the present invention, a method of diagnosing and/or treating a peripheral artery disease in a subject suffering from metabolic disease, wherein automated generation and infusion system comprises Rb-82 generation and infusion system.

In another aspect of the present invention, a method of diagnosing and/or treating a peripheral artery disease in a subject suffering from metabolic disease, wherein the dose of Rb-82 ranges from 0.01 mBq to 10,000 mBq.

In another aspect of the present invention, a method of diagnosing and/or treating a peripheral artery disease in a subject suffering from metabolic disease, wherein the imaging or scanning comprises positron emission tomography imaging.

In another aspect of the present invention, a method of diagnosing and/or treating a peripheral artery disease in a subject suffering from metabolic disease, wherein the region of interest comprises area between abdominal aorta to lower extremities.

In another aspect of the present invention, a method of diagnosing and/or treating a peripheral artery disease in a subject suffering from metabolic disease, wherein the region of interest comprises lower extremities or limbs of the subject.

In another aspect of the present invention, a method of diagnosing and/or treating a peripheral artery disease in a subject suffering from metabolic disease, wherein the scanning technique comprises multi-pass continuous bed motion between abdominal aorta and lower extremities.

In another aspect of the present invention, a method of diagnosing and/or treating a peripheral artery disease in a subject suffering from metabolic disease, wherein the diagnosis comprises determining the presence or absence of peripheral arterial disease in a subject.

In another aspect of the present invention, a method of diagnosing and/or treating a peripheral artery disease in a subject suffering from metabolic disease, wherein the diagnosis comprises identifying a subject at a risk of developing a peripheral arterial disease.

In another aspect of the present invention an imaging protocol for diagnosing a peripheral arterial disease in a subject comprises; a) administering a positron emission tomography agent to the subject; b) performing a single bed positron emission tomography acquisition of the heart for about 1-10 minutes; c) performing a single bed positron emission tomography acquisition of the leg for about 1-10 minutes; d) performing a single bed centered positron emission tomography acquisition at abdominal aorta of the subject for about 1-3 minutes; e) performing continuous bed motion positron emission tomography scan of the subject between abdominal aorta and legs; f) calculating an input function from abdominal artery based on one or more parameters selected from abdominal artery diameter, scanner resolution; and g) calculating the tracer flux into the tissue or region or interest.

In another aspect of the present invention, an imaging protocol for diagnosing a peripheral arterial disease in a subject further comprises performing a computed tomography and/or magnetic resonance imaging of the subject.

In another aspect of the present invention, a method of diagnosing a peripheral arterial disease in a subject suffering from diabetes mellitus comprises: calculating a dose of Rb-82; administering the calculated dose of Rb-82 in a subject at rest and stress condition; image capturing by PET scanner using continuous bed motion shuttle mode; performing quantitative assessment of blood flow in lower extremities or limbs of the subject; performing image analysis and providing a severity score based on the assessment; performing diagnosis or identify the subjects at risk of developing peripheral arterial disease; and generating the report.

BRIEF SUMMARY OF DRAWINGS

FIG. 8A: Representative transaxial rest and hyperemic Rb-82 PET images at mid-calf with muscles segmented.

FIG. 8B: Representative 3D segmentation volumes of interest (VOI) on lower extremity Rb-82 PET images.

FIG. 8C: Averages SUVs in ischemic and non-ischemic limbs for individual muscles.

FIG. 8D: Ratio of ischemic to non-ischemic SUVs at rest and reactive hyperemia.

FIG. 9A: Rb image of a PAD patient during rest and cuff-induced hyperemia showing decreased perfusion in right lower extremity seen during RH.

FIG. 9B: Scatter plots of Rb obtained with heart and abdomen protocol at rest and reactive hyperemia.

FIG. 9C: Regional Rb SUVs at rest and reactive hyperemia.

FIG. 10A: Representative CT muscle segmentation with 82-RB overlay during rest and reactive hyperemia in a PAD patient.

FIG. 10B: A scatter plot demonstrating the reproducibility of using 82-Rb protocols across all 12 participants.

FIG. 10C: The regional 82-Rb SUV differences among various muscle groups in both controls and PAD patients including gastrocnemius (GC), soleus (SOL), tibialis anterior (TA), exterior digitorum longus (EDL) and peroneus (PER) during rest and hyperemia.

DESCRIPTION

Figure 1:
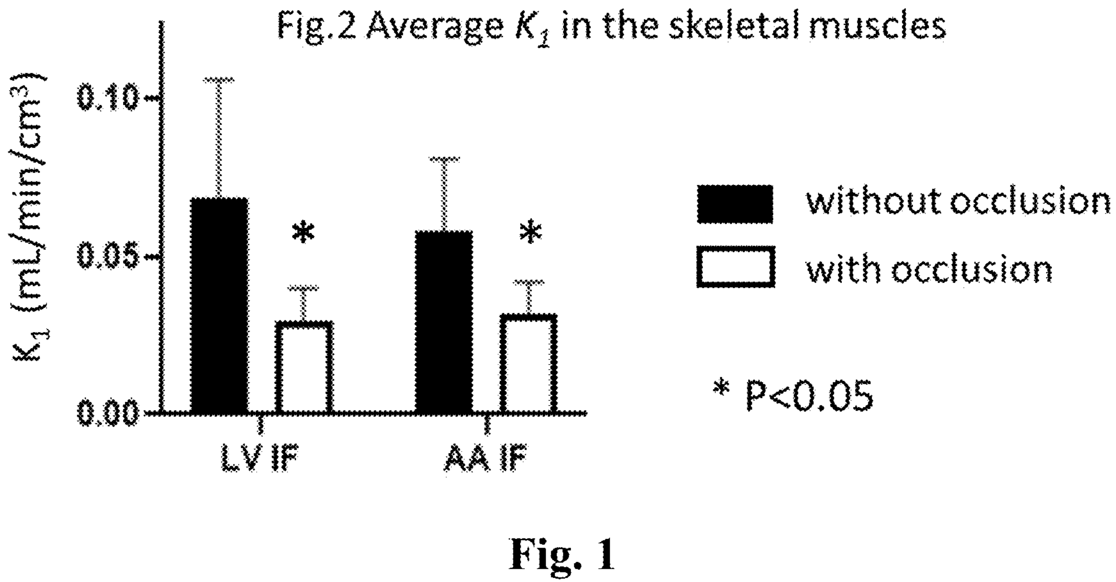
FIG. 1: Average K1 in animal studies in porcine pigs after Rb-82 PET imaging.

There is currently a need to diagnose and treat peripheral arterial disease in subjects suspected or afflicted with the disease. The subjects can be suffering from accompanying conditions like metabolic diseases. The unexpected discovery further provides accurate quantitative assessment of the blood perfusion or blood flow to the affected area or the region of interest.

The present invention can be more readily understood by reading the following detailed description of the invention and included embodiments.

As used herein, the term 'Peripheral Arterial Disease' (PAD) refers to a circulatory problem in which narrowed arteries reduce blood flow to limbs or other part of body. Peripheral arterial disease is a disease of the blood vessels located outside the heart and brain and most often caused by a buildup of fatty deposits in the arteries. PAD affects the blood vessels causing them to narrow, therefore restricting the blood flow to the arms, kidneys, stomach, and most commonly, the legs. Peripheral artery disease is a major risk factor for heart attack and stroke. There are four designated stages of peripheral arterial disease: asymptomatic, claudication, critical limb ischemia and acute limb ischemia. Possible symptoms of peripheral arterial disease include one or more of hair loss on the feet and legs, intermittent claudication, pain in the thigh or calf muscles, leg weakness, cold feeling in foot or leg, numbness, brittle toenails, slow growth of toenails, sores or ulcers on the legs and feet that take a long time to heal, skin on the legs becomes shiny or turns pale or bluish, erectile dysfunction. The most common cause of PAD is atherosclerosis. Atherosclerosis is a steady process in which a fatty material builds up inside the arteries. Less common causes of peripheral artery disease are blood clots in the arteries, injury to the limbs. Risk factors that contribute to PAD are diabetes, smoking, obesity, high blood pressure, increasing age, high cholesterol, family history of heart disease, and excess levels of C-reactive protein or homocysteine. Undiagnosed or untreated PAD can be dangerous; it can lead to painful symptoms, loss of limbs, increased risk of coronary artery disease, and carotid atherosclerosis (a narrowing of the arteries that supply blood to the brain). As people with PAD have an increased risk of heart attack and stroke, the American Heart Association encourages people at risk to discuss PAD with their doctor to ensure early diagnosis and treatment.

As used herein, the term 'metabolic disease' refers to a cluster of conditions that occur together, increasing risk of heart disease, stroke. These conditions include increased blood pressure, diabetes mellitus, excess body fat around the waist, and abnormal cholesterol or triglyceride levels.

As used herein, the term 'diabetes mellitus' refers to a group of metabolic disorders characterized by a high blood sugar level over a prolonged period of time. Symptoms often include frequent urination, increased thirst and increased appetite. If left untreated, diabetes can cause many health complications. Acute complications can include diabetic ketoacidosis, hyperosmolar hyperglycemic state, or death. Serious long-term complications include cardiovascular disease, stroke, chronic kidney disease, foot ulcers, damage to the nerves, damage to the eyes and cognitive impairment. Diabetes occurs due to either the pancreas not producing enough insulin, or the cells of the body not responding properly to the insulin produced. There are three main types of diabetes: a) Type 1 diabetes results from failure of the pancreas to produce enough insulin due to loss of beta cells. This form was previously referred to as 'insulin-dependent diabetes mellitus' (IDDM) or "juvenile diabetes". The loss of beta cells caused by an autoimmune response wherein the cause of autoimmune response is unknown. b) Type 2 diabetes begins with insulin resistance, a condition in which cells fail to respond to insulin properly. As the disease progresses, a lack of insulin can also develop. This form was previously referred to as 'non-insulin-dependent diabetes mellitus' (NIDDM) or 'adult-onset diabetes'. The most common cause is a combination of excessive body weight and insufficient exercise. c) Gestational diabetes is the third main form, and occurs when pregnant women without a previous history of diabetes develop high blood sugar levels.

As used herein, the term 'diagnosis' refers to a process of identifying a disease, condition, or injury from its signs and symptoms. A health history, physical exam, and tests, such as blood tests, imaging, scanning, and biopsies, can be used for diagnosis.

As used herein, the term 'imaging' refers to techniques and processes used to create images of various parts of the human body for diagnostic and treatment purposes within digital health. X-ray radiography, Fluoroscopy, Magnetic resonance imaging (MRI), Computed Tomography (CT), Medical Ultrasonography or Ultrasound Endoscopy Elastography, Tactile imaging, Thermography Medical photography, and Nuclear Medicine Functional Imaging techniques e.g. positron emission tomography (PET) or SPECT (Single-photon emission computed tomography). Imaging seeks to reveal internal structures, as well as to diagnose and treat disease.

As used herein, the term 'Positron Emission Tomography' (PET) refers to a functional imaging technique that uses radioactive substances known as radiotracers or radionuclides to visualize and measure changes in metabolic processes, and in other physiological activities including blood flow, regional chemical composition, and absorption. Different tracers are used for various imaging purposes, depending on the target process within the body commonly used radionuclide tracers for PET imaging include Rb-82 (Rubidium-82), 0-15 (Oxygen-15), F-18 (Fluorine-18), Ga-68 (Gallium-68), Cu-61 (Copper-61), C-11 (Carbon-11), N-13 (Ammonia-13), Co-55 (Cobalt-55), and Zr-89 (Zirconium-89). The preferred radionuclide comprises Rb-82 having a half-life of about 76 seconds.

As used herein, the term SPECT' refers to a Single-photon emission computed tomography is a nuclear medicine tomographic imaging technique using gamma rays. SPECT technique is able to provide three-dimensional (3D) information. The technique needs delivery of a gamma-emitting radioisotope (a radionuclide) into the patient, normally through injection into the bloodstream. Many times though, a marker radioisotope attached to a specific ligand to create a radioligand, whose properties bind it to certain types of tissues. This allows the combination of ligand and radiopharmaceutical to be carried and bound to a region of interest in the body, where the ligand concentration assessed by a gamma camera. SPECT agents include $^{99}$mTc, $^{123}$I, $^{131}$I, $^{111}$In, $^{155}$Tb and $^{133}$Xe.

As used herein, the term 'Computed Tomography' (CT) refers to a computerized x-ray imaging in which a beam of x-rays aimed at a patient and rotated around the body, producing signals that are processed by the machine's computer to generate cross-sectional images of the body. These slices are called tomographic images and contain detailed information than conventional x-rays. Once the machine's computer collects a number of successive slices, they can be digitally "stacked" together to form a three-dimensional image of the patient that allows for easier identification and location of basic structures as well as possible tumors or abnormalities.

As used herein, the term 'Magnetic Resonance Imaging' (MRI) is a non-invasive imaging technology that produces 3D detailed anatomical images, which is used for disease detection, diagnosis, and treatment monitoring. MRI is based on technology that excites and detects the change in the direction of the rotational axis of protons found in the water that makes up living tissues.

As used herein, the term 'automated generation and infusion system' refers to system for generation and/or infusion of a radionuclide or radiotracer and administration into a subject. The automated infusion system comprises radioisotope generator, dose calibrator, computer, controller, display device, activity detector, cabinet, cart, waste bottle, sensors, shielding assembly, alarms or alerts mechanism, tubing, source vial, diluent or eluant, valves. The automated infusion system can be communicatively or electronically coupled to imaging system.

As used herein, the term 'continuous bed motion scan' (CBM) refers to continuous motion of the patient bed during the acquisition of PET images. This PET acquisition mode is similar to the whole body CT scan in which the patient bed moves continuously through the scanner. The advantages of continuous bed motion scan include uniform axial signal-to-noise ratio, elimination of resolution artifacts by sampling continuously in the axial direction and a reduction in noise from detector normalization. The technologist can tailor the protocols according to each individual organ to perform a personalized exam for patient's individual needs. This is different from the conventional method where PET images are acquired with sequential bed positions, alternating between image acquisition and patient table motion. Continuous bed motion scan provides personalized exam protocols based on patient anatomy, definition up to four distinct scanning regions, each with a different bed speed, high-resolution reconstructions, simple protocol setup.

As used herein, the term 'assessment' refers to a qualitative or quantitative assessment of the blood perfusion in a body part or region of interest. The quantitative assessment comprises kinetic compartment model or retention model for quantitative assessment of blood perfusion or flow in the region of interest.

As used herein, the term 'non-invasive' refers to, when no tools enter into the body of the subject.

As used herein, the term 'stress agent' refers to agents used to generate stress in a patient or a subject during imaging procedure. The stress agents according to the present invention are selected from regadenoson, dobutamine, adenosine, and dipyridamole. Alternatively, stress can be induced by exercise without use of stress agent depending on the subject condition.

As used herein, the term 'dose' refers to the dose of radionuclide required to perform imaging in a subject. The dose of a radionuclide to be administered into the subject ranges from 0.01 mBq to 10,000 mBq.

As used herein, 'predetermined threshold value' refers to a threshold value of blood perfusion in normal subjects or non-occluded tissues or arteries.

In an embodiment, the present invention provides a method of diagnosing peripheral arterial disease in a subject comprising performing a PET scan, PET/CT scan, SPECT scan, PET/MRI scan, Mill scan or combinations thereof by administering a PET agent, a SPECT agent, a contrast agent, and a dye or combinations thereof.

In an embodiment according to the present invention, peripheral arterial disease comprises limb ischemia, plaque formation, atherosclerosis, inhibited or decreased blood perfusion or blood flow to any body part, preferably limbs or lower extremities.

In an embodiment, the present invention provides the imaging protocols for diagnosing a peripheral arterial disease in a subject. Imaging protocols are based on PET, SPECT CT, MM or combinations thereof. In an embodiment, the PET imaging comprises PET dynamic imaging using multi-pass continuous bed motion (CBM).

In an embodiment, the radionuclide is selected from PET or SPECT agent. The PET or SPECT agent can be radiolabeled with one or more ligands or can be administered without radiolabeling.

In another embodiment, the radionuclide is attached to the ligand before administration into the subject. The ligands are provided in suitable dosage form and radionuclide is attached to the ligand and then administered into the subject for imaging. The ligands according to the present invention can be selected from Tetrofosmin, Sestamibi, and Fluorodeoxyglucose.

In an embodiment, PET agents can be selected from Rb-82 (Rubidium-82), O-15 (Oxygen-15), F-18 (Fluorine-18), Ga-68 (Gallium-68), Cu-61 (Copper-61), C-11 (Carbon-11), N-13 (Ammonia-13), Co-55 (Cobalt-55), and Zr-89 (Zirconium-89); preferably Rb-82 (Rubidium-82).

In an embodiment, SPECT agents can be selected from $^{99}$mTc, $^{123}$I, $^{131}$I, $^{111}$In, $^{155}$Tb, $^{201}$Tl and $^{133}$Xe.

In an embodiment, the present invention provides a method of reliably detecting peripheral arterial disease in a subject comprising: a) administering Rb-82 chloride to a subject using automated rubidium elution system; b) performing a multipass shuttle mode scanning technique between abdominal aorta and lower extremities; c) diagnosing peripheral arterial disease in a subject.

In an embodiment, the present invention provides a method of carrying out a non-invasive personalized screening test comprising: a) acquiring the data from the patient using automated generation and infusion system, preferably rubidium-82 generation and elution system; b) measuring the blood flow, pressure and pulse; c) recording an image of at least one body zone or region of interest of the subject; d) analyzing the data and image to determine type, location and staging of peripheral arterial disease.

In an embodiment, the present invention provides a method of determining whether a subject is suffering from a peripheral arterial disease comprising: a) administering into the subject a radionuclide and/or stress agent; b) performing one or more imaging scans of the subject; c) determining, by analysis of the one or more images, quantitative assessment of blood perfusion or flow in a region of interest in the subject; d) comparing the perfusion in the region of interest in the subject to a predetermined threshold value; and e) classifying the subject as having the peripheral arterial disease or as not having the peripheral arterial disease based on the comparison of step d); and f) determining whether the subject is suffering with peripheral arterial disease or not.

In an embodiment, the present invention provides method of determining whether a subject is suffering with a peripheral arterial disease comprising: a) administering into the subject rubidium-82 and/or stress agent; b) performing one or more PET imaging scans of the subject; c) determining, by analysis of the one or more PET images, quantitative assessment of blood perfusion or flow in a region of interest in the subject; d) comparing the perfusion in the region of interest in the subject to a predetermined threshold value; and e) classifying the subject as having the peripheral arterial disease or as not having the peripheral arterial disease based on the comparison of step d); and f) determining whether the subject is suffering with peripheral arterial disease or not.

In another embodiment, the present invention provides method of preparing a report categorizing a subject as having a peripheral arterial disease or as not having a peripheral arterial disease comprising: a) receiving the data of one or more imaging scans of the subject performed by a imaging device after a radionuclide was administered into the subject; b) processing the data to determine blood perfusion for the region of interest in the subject and comparing the perfusion value to a predetermined threshold value; and c) populating a report categorizing the subject as having or not having peripheral arterial disease or at a risk of developing a peripheral arterial disease.

The present invention further provides a method of treating a subject suffering with a peripheral arterial disease comprising: a) determining whether the subject is suffering from the peripheral arterial disease comprising: (i) administering into the subject a radionuclide and/or a stress agent; (ii) performing one or more imaging scans of the subject; (iii) determining, by analysis of the one or more obtained images (iv) performing quantitative assessment of blood perfusion or flow; (v) comparing the perfusion value in the region of interest in the subject to a predetermined threshold value; and (vi) categorizing the subject as afflicted with the peripheral arterial disease when the perfusion value of the radionuclide in the subject is lower than the predetermined threshold value; and (b) treating the subject based on the determination obtained in step (a).

The present invention further provides a method of treating a subject suffering with a peripheral arterial disease comprising: (a) determining whether the subject is suffering with the peripheral arterial disease comprising: (i) administering into the subject rubidium-82 and/or a stress agent; (ii) performing one or more PET imaging scans of the subject; (iii) determining, by analysis of the one or more obtained PET images (iv) performing quantitative assessment of blood perfusion or flow; (v) comparing the perfusion value in the region of interest in the subject to a predetermined threshold value; and (vi) categorizing the subject as afflicted with the peripheral arterial disease when the perfusion value in the subject is lower than the predetermined threshold value; and (b) treating the subject based on the determination obtained in step (a).

In another embodiment, method of treating a subject diagnosed with peripheral arterial disease or at risk of developing peripheral arterial disease comprises revascularization, cholesterol lowering medications, blood pressure control medications, blood sugar control medications, blood clot preventing medications, symptoms relieving medications, smoking cessation medications, surgery, amputation or life style management including but not limited to exercise, healthy diet, nutrition supplements or combinations thereof.

In an embodiment, the present invention provides accurate quantitative assessment of the peripheral arterial disease based on blood perfusion to the affected body part. The assessment is based kinetic compartment model or retention model for quantitative assessment of perfusion in patients.

In an embodiment, the subject is a human subject.

In an embodiment, the human subject is a male or female subject.

In an embodiment, the subject can be suffering from additional disease like metabolic disease.

In an embodiment, the additional disease is diabetes mellitus.

In an embodiment, the PET radionuclide is introduced by injection or infusion into the bloodstream of the subject. In a preferred embodiment, radionuclide is administered via automated generation and/or infusion system.

In an embodiment, pharmaceutical compositions are provided comprising imaging agent. The composition can comprise radionuclide or radionuclide labelled to ligand and/or one or more excipient. In another embodiment, the ligand can be labelled or unlabeled. In additional embodiment, the radionuclide for administration to the subject comprising Rb-82 generated by automated generation and infusion system comprising on-board strontium rubidium generator. The system automatically pumps the eluant from the source into the generator or column comprising bound Sr-82 and elutes Rb-82 in a form of Rb82-Cl, which is then infused/administered into patient after activity measurements. In other embodiments, the imaging agent having longer half-life can be produced at other location and can be placed as a bulk solution in automated infusion system for administering into a subject with or without further dilution. In still another embodiment, the imaging agent can be prepared in a radiopharmacy or manufacturing location and can be transported to administration location or diagnostic center or hospital in a suitable container like syringes, vials, ampoules, pre-filled syringes. The composition can be presented in a kit comprising one or more containers with radionuclide in a shielded container. The pharmaceutical compositions of the present invention can be in the form of lyophilized powder, liquids, and suspensions.

In an embodiment, the method of diagnosing/imaging a region of interest of a subject comprising; a) input one or more subject parameters; b) calculating the appropriate dose of rubidium-82 based; c) generating a dose of Rb-82 from rubidium elution system; d) administering Rb-82 and/or stress agent to the subject in need thereof; e) performing PET scanning of the region of interest; f) quantitative assessment of the blood flow in the region of interest; g) generating a report of the assessment.

A method of diagnosing a peripheral arterial disease in a subject suffering from diabetes mellitus comprises: a) calculating a dose of Rb-82; b) administering the calculated dose of Rb-82 in a subject at rest and stress condition; c) image capturing by PET scanner using continuous bed motion shuttle mode; d) performing quantitative assessment of blood flow in lower extremities or limbs of the subject; e) performing image analysis and providing a severity score based on the assessment; f) performing diagnosis or identify the subjects at risk of developing peripheral arterial disease; and g) generating the report.

In another embodiment of the present invention, features of imaging are provided comprising; administering personalized single "rest" Rb-82 chloride dose protocol and start imaging; administering a pharmacologic stress agent and second dose protocol after resting dose infusion; scanning technique consists of multi pass continuous bed motion with back and forth shuttling between abdominal aorta and lower extremities; validating derived quantitative flow with 0-15 water imaging; the protocol provides improved granularity of abnormal images; measuring of relative image changes over time to report on peripheral arterial disease progression.

In an embodiment, the assessment is based on lower extremities perfusion at rest, along with perfusion reserve in response to pharmacological stress or exercise induced stress. In an embodiment, the assessment can be qualitative or quantitative.

In an embodiment according to the present invention, input function may be required for quantitative assessment of blood flow to the region of interest or tissue. An input function can be calculated by using non-invasive imaging method and is validated by blood sampling method. The arterial blood activity was continuously sampled as gold standard input function.

In an embodiment, the predetermined radionuclide uptake potential or blood flow or perfusion threshold value is calculated as K1, which is based on blood perfusion as volume per unit time per unit volume of the tissue. The threshold value is calculated in comparison to the occluded tissues to normal tissues or unoccluded tissues. The threshold value can range from 0.01 to 1.5.

In some embodiments, diagnosis of peripheral arterial disease further comprises carrying out one or more computed tomography (CT) scans of the subject.

In some embodiments, diagnosis of peripheral arterial disease further comprises carrying out one or more magnetic resonance imaging (Mill) scans of the subject.

In another embodiment, the present invention provides a method of determining whether a subject is at risk for developing a peripheral arterial disease or not.

The present invention provides a method of determining whether a subject is at risk for developing a peripheral arterial disease comprising: a) administering into the subject a rubidium-82 radionuclide and/or stress agent; b) performing one or more PET imaging scans of the subject; c) determining, by analysis of the one or more images, blood perfusion or flow in the region of interest; d) performing quantitative assessment of blood perfusion or flow to a predetermined threshold value; and e) categorizing the subject as at risk for developing the peripheral arterial disease or as not at risk for developing the peripheral arterial disease based on the comparison of step d) thereby determining whether the subject is at risk for developing the peripheral arterial disease or not.

In an embodiment, the imaging protocol comprises; a) administering a PET agent to the subject; b) single bed PET acquisition of the heart for about 1-10 minutes, preferably for about 1-8 minutes, more preferably for about 2-7 minutes; c) single bed PET acquisition of the leg for about 1-10 minutes, preferably for about 1-8 minutes, more preferably for about 2-7 minutes; d) single bed centered PET acquisition at abdominal aorta of the subject for about 1-3 minutes; e) continuous bed motion PET scan of the subject between abdominal aorta and legs; f) input function is calculated from abdominal artery having a consistent recovery coefficient based on one or more parameters like abdominal artery diameter, scanner resolution; g) calculating the tracer flux into the tissue or region or interest (K1); h) optionally performing a CT scan of the subject during method.

In some embodiments, the predetermined threshold value is determined by analyzing a control subject or group of control subjects that are not suffering with a peripheral arterial disease and/or diabetes mellitus.

In the present application, all numbers disclosed herein can vary by 1 percent, 2 percent, 5 percent, or up to 20 percent if the word "about" is used in connection therewith. This variation can be applied to all numbers disclosed herein.

Each embodiment disclosed herein is contemplated as being applicable to each of the other disclosed embodiments. Thus, all combinations of the various elements described herein are within the scope of the invention.

This invention will be better understood by reference to the experimental data which follow, but those skilled in the art will readily appreciate that the specific experiments detailed are only illustrative of the invention as described more fully in the claims which follow thereafter.

Experiments

In these experiments, Rb82-Cl was generated using automated generation and infusion system having on-board Sr—Rb generator. Appropriate dose of Rb-82 was calculated by the system. After dose calculation, the system automatically instructs the controller to pump eluant (sodium chloride) from the eluant source and generate a calculated dose of Rb-82, which is administered to a subject via infusion system. Imaging scans were performed using the imaging system. Similarly, images were obtained after administering stress agent into the subject. Qualitative and quantitative assessment was performed depending on the blood perfusion in the region of interest and severity score is provided for each subject. Based on the assessment, if the subject is found suffering from peripheral arterial disease or at risk of developing a peripheral arterial disease, suitable therapy options are provided.

Animal Studies

Example 1

Figure 4:
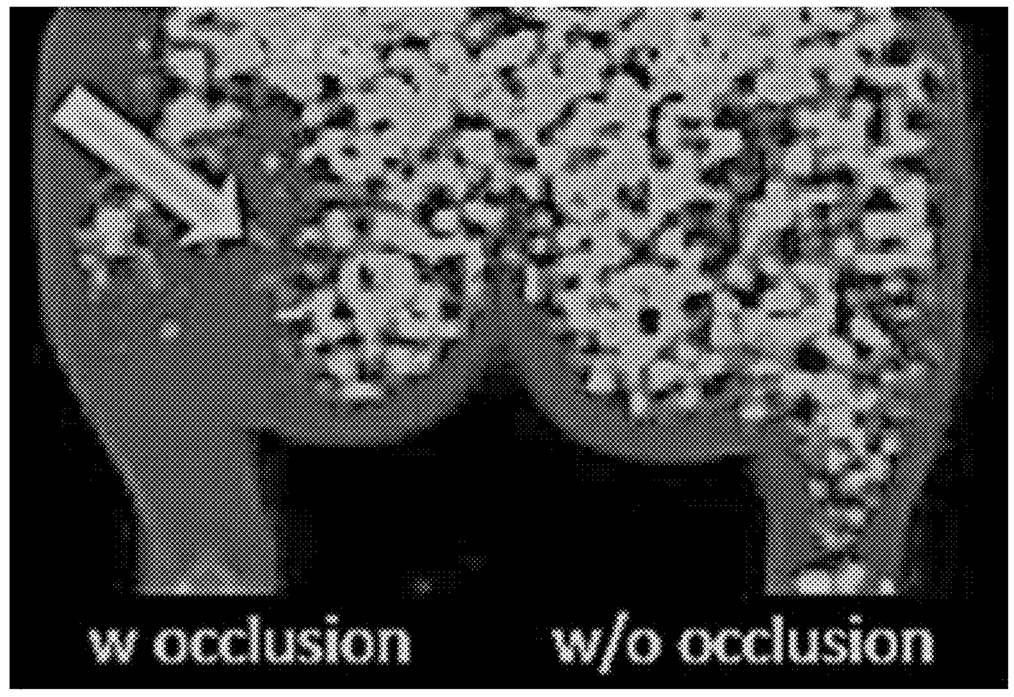
FIG. 4: Represents the sample animal K1 parametric image with AA as the input function.
Figure 6:
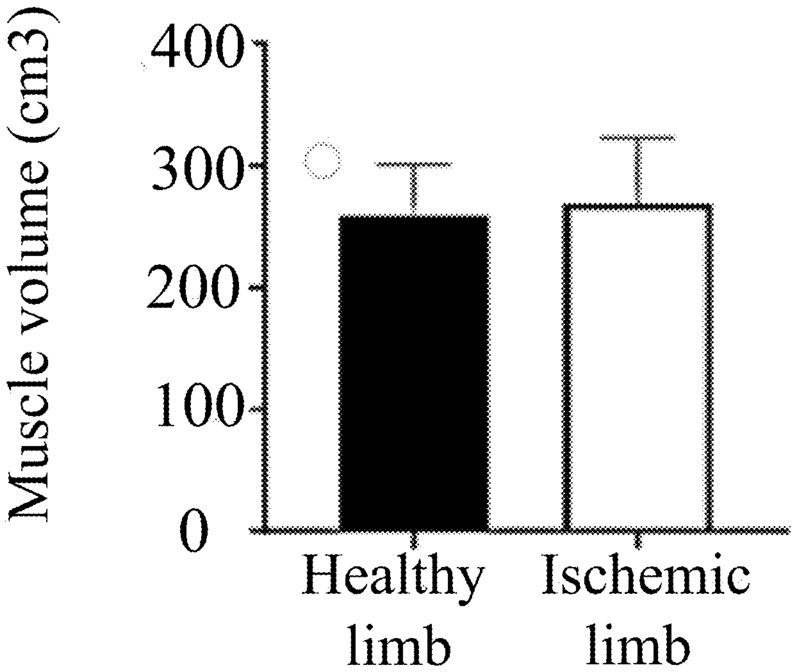
FIG. 6: Represents the muscle volumes in animal studies.

CT scan was performed on the subject for standard attenuation correction, and multi-energy low dose contrast CT imaging was performed to define the lower extremity vasculature and attenuation correction was performed using virtual non-contrast images; 518±37 MBq Rb-82 was administered to the subject using automated generation and infusion system; single bed PET acquisition of the heart for about 1-10 minutes, was performed; single bed PET acquisition of the leg for about 1-10 minutes was performed; single bed centered PET acquisition at abdominal aorta of the subject for about 1-3 minutes was performed; continuous bed motion PET scan of the subject between abdominal aorta and legs was performed; tracer flux (K1) into the tissue or region of interest is calculated as volume per unit time per unit volume of tissue. Average K1 was found to be less than 0.05 ml/min/cm$^3$ in occluded tissue in comparison to non-occluded tissue (FIG. 1). It was validated by injecting microspheres over 30 seconds during the PET imaging at either rest or stress conditions for each animal and blood flow was measured in both gastrocnemius and soleus muscles. FIG. 4 represents the sample animal K1 parametric image with AA as the input function. FIG. 6 represents the muscle volumes in animal studies.

Example 2

Introduction: The distribution and control of skeletal muscle perfusion (SMP) and perfusion reserve (SMPR) has implications in management of peripheral artery disease (PAD). Rb-82 PET enables detection of muscle specific changes in SMP and SMPR with imaging at rest and during cuff-Induced hyperemia (CIH).

Methods: Hindlimb ischemia (HLI) was created in rabbits (n=8) by right femoral ligations and Rb-82 PET/CT imaging performed on digital PET scanner (Vision600, Siemens) at either 2 or 4 weeks post-ligation. Rabbits were injected with Rb-82 (1.5 mCi) with constant activity infusion over 30 seconds at rest and 30 seconds following hyperemia induced by 3 minutes cuff occlusion of thighs bilaterally. PET images were acquired with shuttling scanner from heart to feet using 8 passes over 7 minutes. Summed images were created excluding the first 90 seconds post injection. Calf muscles were segmented based on CT images. Mean Rb-82 standardized uptake values (SUVs) were calculated for calf muscles—gastrocnemius (GC), plantaris (PLA), soleus (SOL), tibialis anterior (TA), extensor digitorum longus (EDL), peroneus (PER)—for both ischemic (I) and non-ischemic (NI) limbs. CT angiography was performed, and tissues analyzed for fiber type and capillary density.

Results: Representative images and VOIs are shown (FIG. 8*a-b*). Rb-82 imaging identified differences in SMP at both rest and CIH among individual muscles (p-value<0.05, FIG. 8*c*). No significant difference was observed at rest in SUVs between I and NI limbs across muscles (0.55±0.18, 0.51±0.16, p=0.16). Significant differences were observed in SMP SUVs with CIH between limbs (I: 1.02±0.32, NI:1.14±0.34, p<0.01). SMPR was impaired in I limb (1:1.98±0.63, NI: 2.30±0.54, p=0.01) in presence of collaterals. FIG. 8*d* illustrates the ratio of ischemic to non-ischemic SUVs at rest and reactive hyperemia.

Conclusion: The study demonstrated that RB-82 imaging can identify regional differences in SMP and SMPR across calf muscles at rest and CIH. In a chronic model of HLI with collateralization CIH was more sensitive in detecting obstructive vascular disease.

Human Study

Example 3

Figure 2:
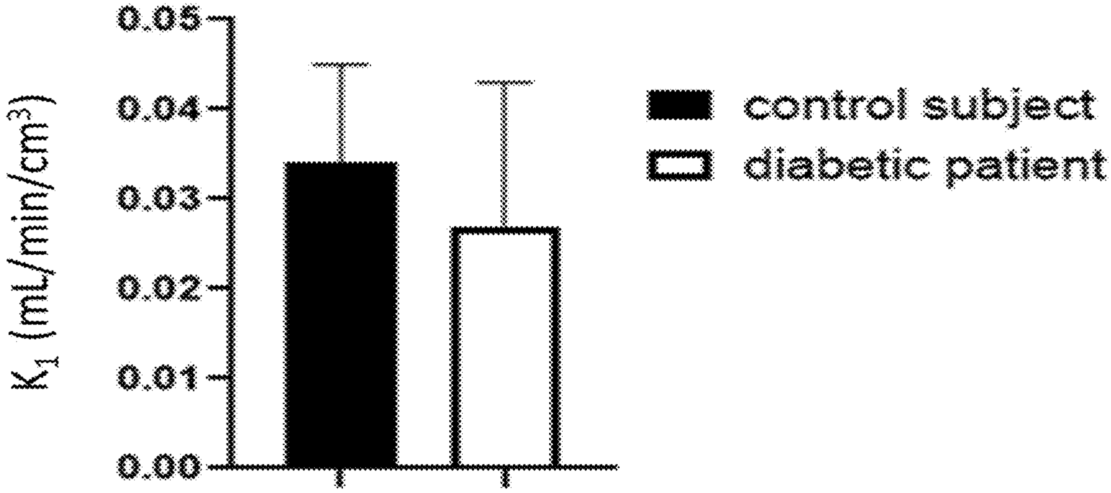
FIG. 2: Average K1 in human studies after Rb-82 PET imaging.
Figure 3:
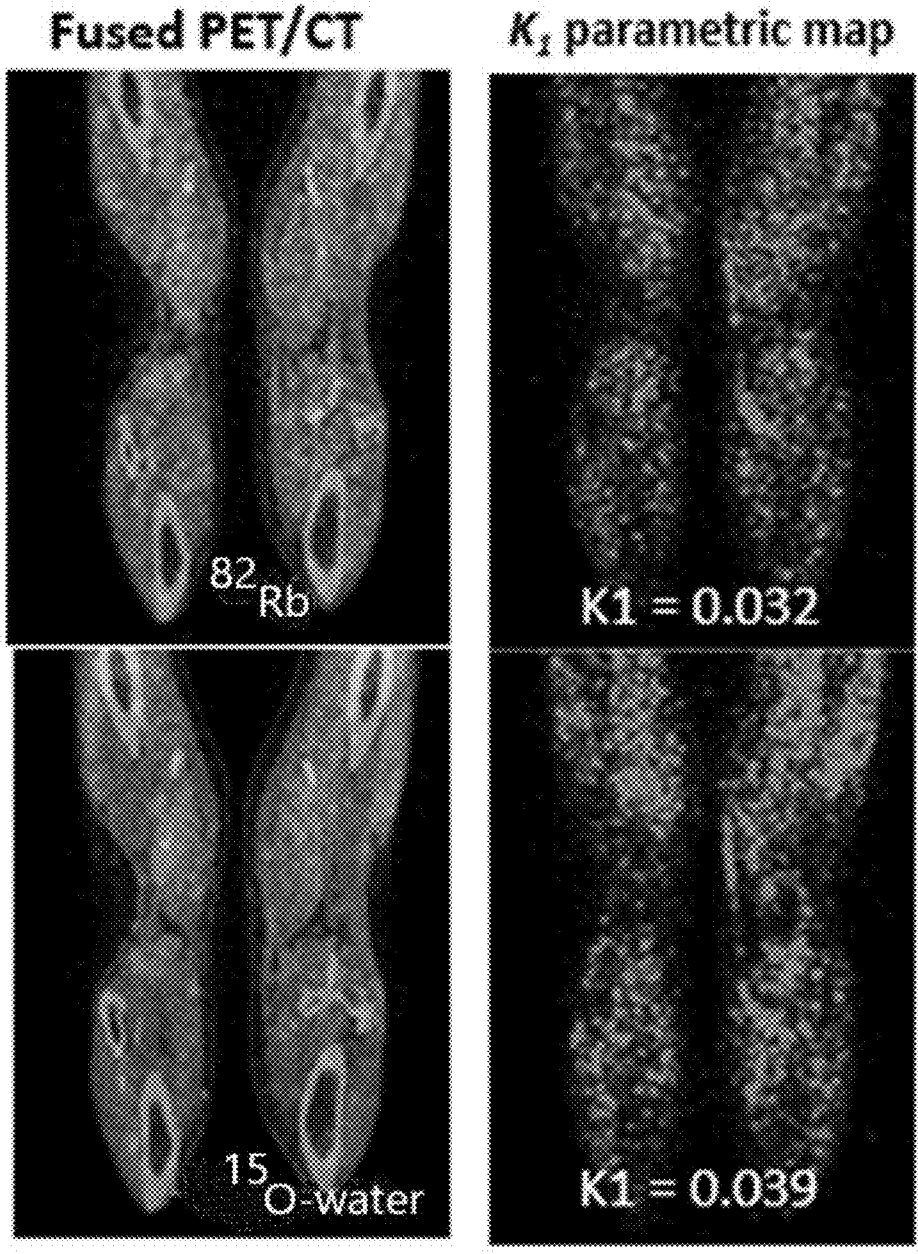
FIG. 3: Validation of Rb-82 PET imaging protocols with $^{15}O$ water.
Figure 5:
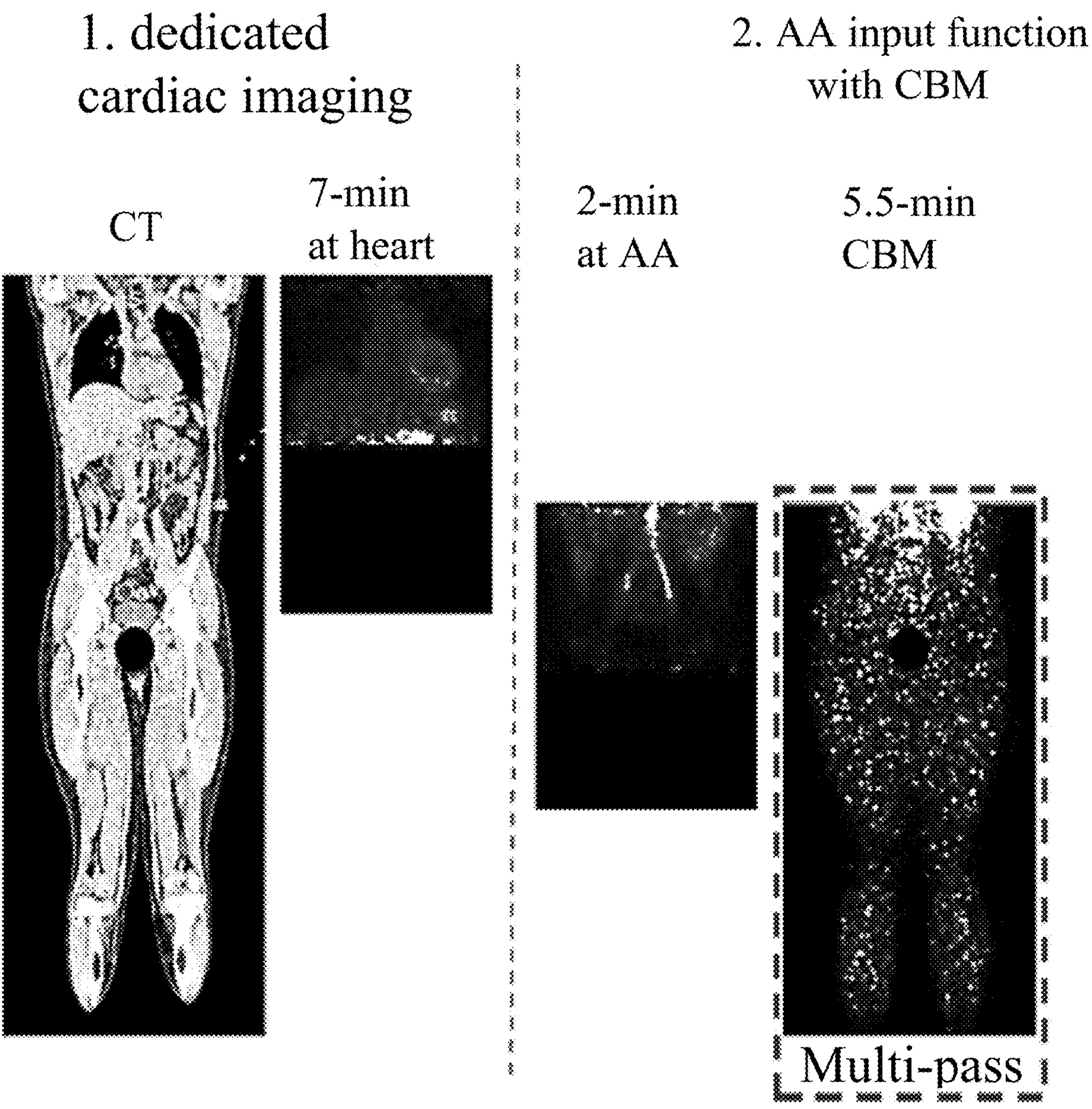
FIG. 5: Represents the image acquisition protocol during human study.
Figure 7:
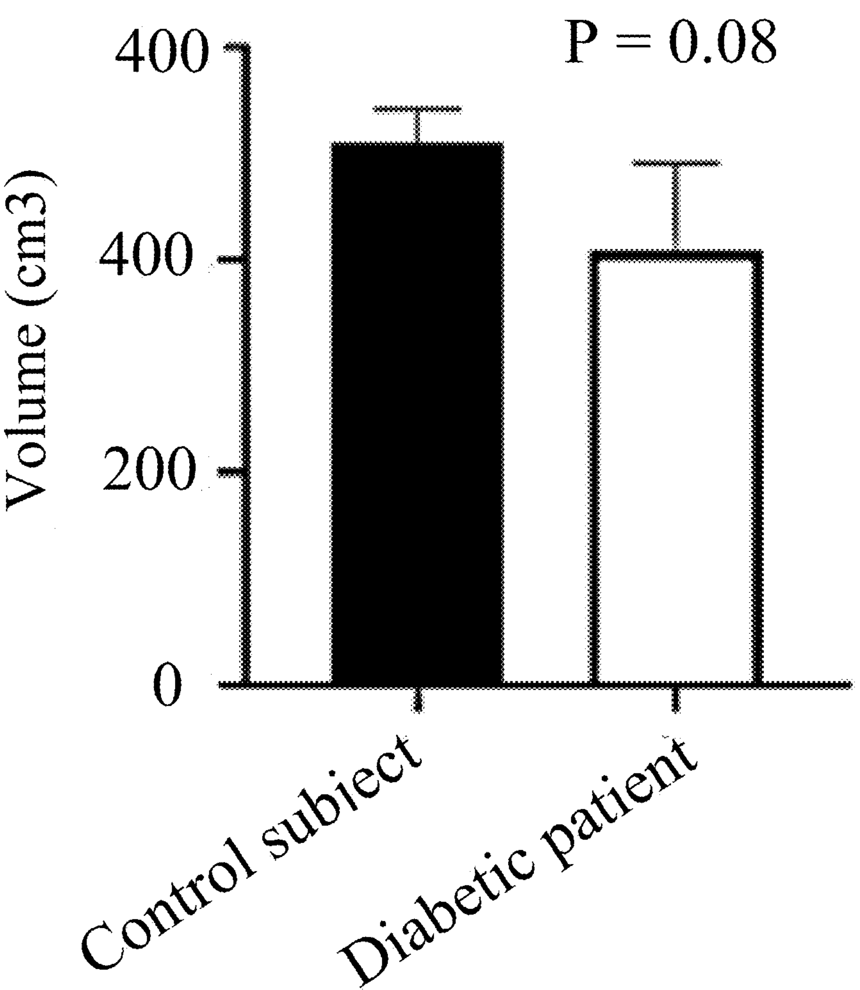
FIG. 7: Represents the muscle volumes in human studies.

CT scan was performed on the subject for standard attenuation correction, multi-energy low dose contrast CT imaging was performed to define lower extremity vasculature and attenuation correction was performed using virtual non-contrast images; 518±37 MBq Rb-82 is administered to the subject using automated generation and infusion system agent; single bed PET acquisition of the heart for about 2-7 minutes is performed; single bed centered PET acquisition at abdominal aorta of the subject for about 1-3 minutes is performed; continuous bed motion PET scan of the subject between abdominal aorta and legs is performed; input function was calculated from abdominal artery; Tracer flux (K1) into the tissue or region of interest is calculated as volume per unit time per unit volume of tissue. Average K1 was found to be less than 0.05 ml/min/cm$^3$ in occluded tissue in comparison to non-occluded tissue (FIG. 2). Rb-82 parametric imaging was validated in a diabetic subject by $^{15}$O-water parametric imaging, 3D region of interest on the low limb was drawn and the average K1 value with Rb-82 was found to be 0.032 in comparison to 0.039 with $^{15}$O-water (FIG. 3). FIG. 5 represents the image acquisition protocol during human study. FIG. 7 represents the muscle volumes in human studies.

Example 4

Introduction: As discussed herein, peripheral artery disease (PAD) affects both large vessels and the microcirculation. The standard clinical test, ankle brachial index (ABI), is insensitive for detection of microvascular disease. This experiment evaluated the normal distribution of lower extremity perfusion and perfusion reserve using rubidium-82 (Rb) positron emission tomography (PET) in healthy controls and patients with a spectrum of PAD.

Method: Rb PET/CT imaging (Vision600, Siemens) was performed in control subjects (n=6) and PAD patients (n=6). Rb (20-30 mCi) was delivered using a constant activity infusion over −30 s, with PET images acquired with shuttling scanner from either heart (Protocol 1) or abdomen (Protocol 2) to feet using 8-11 passes over 7 minutes. The abdominal protocol was repeated 30 seconds after reactive hyperemia (RH) induced by 5 minutes bilateral thigh cuff occlusion. Regional Rb standardized uptake values (SUVs) were calculated at the level of thigh, calf, and foot (FIG. 9A) and compared to ABIs.

Results: Regional lower extremity Rb SUV values were reproducible at rest ($R^2$=0.96, FIG. 9B). There was no significant difference in Rb SUVs in thigh and calf between control and PAD patients at rest, although foot SUVs were significantly higher in PAD patients versus controls (FIG. 9C, P<0.05). There was a significant increase in thigh Rb RH SUV in controls subjects (p<0.05) with a trend towards an increase in PAD patients (p=0.06). A significant (p<0.05) increase in calf perfusion during RH was seen only in PAD patients but not controls. There were no significant differences in the feet. SUVs at the level of the foot did not correlate with ABIs (r=0.01).

Conclusion: Rb PET provided a reproducible estimate of regional gradients in lower extremity perfusion. PAD patients exhibited a different pattern compared to controls at rest and during cuff-induced hyperemia. Evaluation of RH with Rb PET provides unique information about the microcirculation not provided by ABIs.

Example 5

Introduction: This study aimed to examine the reproducibility of rubidium-82 (Rb) positron emission tomography (PET) imaging at rest and during reactive hyperemia (RH) for evaluation of calf muscle perfusion (CMP) in healthy controls and patients with varying stages of peripheral artery disease (PAD) using an innovative acquisition protocol.

Methods: Rb PET/CT imaging (Vision600, Siemens) was performed in healthy controls (n=6) and PAD patients (n=6). Rb (20-30 mCi) was delivered using a constant activity infusion over −30 s, with PET images acquired by shuttling scanner from either heart (Protocol 1) or abdomen (Protocol 2) to feet using 8-11 passes over 7 minutes. Abdominal protocol was repeated 30 seconds after RH induced by 5 minutes bilateral thigh cuff occlusion. Mean Rb standardized uptake values (SUV), excluding the input function, were determined for calf muscles segmented in both legs using hybrid CT images including: gastrocnemius (GC), soleus (SOL), tibialis anterior (TA), extensor digitorum longus (EDL), and peroneus (PER) (FIG. 10A).

Results: Rest Rb SUV were highly reproducible between acquisition methods ($R^2$=0.88, Pearson=0.90, FIG. 10B). For the classic glycolytic (GC) and oxidative (SOL) muscles there was a trend for increased perfusion in SOL in controls (GC: 0.44±0.11, SOL: 0.52±0.12) and PAD subjects (GC: 0.50±0.11, SOL: 0.66±0.20) (FIG. 10C). PAD patients exhibited greater uptake in calf muscles perfusion during RH of 0.96±0.58 (GC) and 1.08±0.76 (SOL) compared to controls 0.38±0.18 (GC) and 0.34±0.14 (SOL) (P value<0.05 for SOL). There were no adverse effects associated with cuff occlusions.

Conclusion: The study demonstrated a novel and safe use of Rb PET imaging for assessing CMP at rest and RH along with establishing reproducibility in control and PAD subjects. There was higher uptake of Rb during RH in PAD patients vs controls. To the extent necessary, further studies can further define the pathophysiology and potential clinical applications of Rb PET imaging in evaluating vascular reactivity in PAD.

The experiments and technical data of the present invention establish that it is feasible to quantify skeletal muscle blood flow in the lower extremities using dynamic Rb-82 PET in both animal and human studies. Inventors of the present invention surprisingly found that optimal data acquisition protocols that take advantage of CBM, constant activity infusion, and an image derived input function, and tracer kinetic modeling methods established to ensure accurate and reproducible quantification of lower extremities flows in determining peripheral arterial disease (PAD).

What is claimed:

1. A method of diagnosing and/or treating a peripheral artery disease in a subject suffering from metabolic disease comprising:

a) calculating a dose of Rb-82 chloride to be administered to the subject;

b) administering the calculated dose of Rb-82 chloride to the subject by an automated generation and infusion system and scanning a region of interest;

c) administering a pharmacologic stress agent and second dose protocol after resting dose infusion and scanning the region of interest;

d) performing an assessment of images using continuous bed motion shuttle mode; and e) diagnosing peripheral arterial disease in the subject thereof;

wherein the continuous bed motion shuttle mode is performing:

i) a single bed positron emission tomography acquisition of the heart for about 1-10 minutes;

ii) a single bed positron emission tomography acquisition of the leg for about 1-10 minutes;

iii) a single bed centered positron emission tomography acquisition at abdominal aorta of the subject for about 1-3 minutes;

iv) continuous bed motion positron emission tomography scan of the subject between abdominal aorta and legs;

v) calculating an input function from abdominal artery based on one or more parameters selected from abdominal artery diameter and scanner resolution; and vi) calculating the tracer flux (K1) into the tissue or region of interest;

wherein the tracer flux (K1) is less than 0.05 ml/min/$cm^3$ in occluded tissue in comparison to non-occluded tissue and is associated with peripheral arterial disease.

2. The method according to claim 1, wherein the metabolic disease is diabetes mellitus.

3. The method according to claim 1, wherein automated generation and infusion system comprises Rb-82 generation and infusion system.

4. The method according to claim 1, wherein the dose of Rb-82 ranges from 0.01 mBq to 10,000 mBq.

5. The method according to claim 1, wherein the assessment of images using continuous bed motion shuttle mode comprises positron emission tomography imaging.

6. The method according to claim 1, wherein the region of interest comprises area between abdominal aorta to lower extremities.

7. The method according to claim 1, wherein the region of interest comprises lower extremities or limbs of the subject.

8. The method according to claim 1, wherein the scanning technique comprises multi-pass continuous bed motion between abdominal aorta and lower extremities.

9. The method according to claim 1, wherein the diagnosis comprises determining the presence or absence of the peripheral arterial disease in the subject.

10. The method according to claim 1, wherein the diagnosis comprises identifying the subject at a risk of developing the peripheral arterial disease.

11. The method according to claim 1, wherein the protocol further comprises performing a computed tomography and/or magnetic resonance imaging of the subject.

12. The method according to claim 1, further comprising:

a) calculating a dose of Rb-82;

b) administering the calculated dose of Rb-82 in the subject at rest and stress condition;

c) image capturing by PET scanner using continuous bed motion shuttle mode;

d) performing quantitative assessment of blood flow in lower extremities or limbs of the subject;

e) performing image analysis and providing a severity score based on the assessment;

f) performing diagnosis or identify the subjects at risk of developing peripheral arterial disease; and g) generating a report.

13. The method according to claim 1, wherein the calculated dose of Rb-82 uptake potential or blood flow or perfusion threshold value is calculated as K1, which is based on blood perfusion as volume per unit time per unit volume of the tissue.

14. The method according to claim 13, wherein the threshold value is calculated in comparison to the occluded tissues to normal tissues or unoccluded tissues.

15. The method according to claim 14, wherein the threshold value can range from 0.01 to 1.5.

16. The method according to claim 1, further comprising validating the tracer flux (K1), wherein the tracer flux (K1) is validated by injecting microspheres over 30 seconds during the positron emission tomography imaging at rest or stress conditions and blood flow is measured in gastrocnemius and soleus muscles.

* * * * *